(12) United States Patent
Mueller

(10) Patent No.: US 9,566,130 B2
(45) Date of Patent: Feb. 14, 2017

(54) SYSTEM FOR DENTAL CLEANING

(75) Inventor: Daniel Mueller, Burgstall (IT)

(73) Assignee: Dental Care Innovation GmbH (DE)

( * ) Notice: Subject to any disclaimer, the term of this patent is extended or adjusted under 35 U.S.C. 154(b) by 0 days.

(21) Appl. No.: 13/294,837

(22) Filed: Nov. 11, 2011

(65) Prior Publication Data
US 2012/0141953 A1 Jun. 7, 2012

Related U.S. Application Data

(63) Continuation of application No. PCT/IB2011/000576, filed on Mar. 19, 2011.

(30) Foreign Application Priority Data

Nov. 12, 2010 (DE) .......................... 10 2010 051 225
Nov. 12, 2010 (DE) .......................... 10 2010 051 226
Nov. 12, 2010 (DE) .......................... 10 2010 051 227

(51) Int. Cl.
*A61C 3/02* (2006.01)
*A61C 3/025* (2006.01)
*B05B 1/34* (2006.01)
*B05B 7/24* (2006.01)
*B24C 5/04* (2006.01)
*A61C 17/02* (2006.01)

(52) U.S. Cl.
CPC .............. *A61C 3/025* (2013.01); *B05B 1/3426* (2013.01); *B05B 1/3442* (2013.01); *B05B 1/3447* (2013.01); *B05B 7/2462* (2013.01); *B24C 5/04* (2013.01); *A61C 17/02* (2013.01)

(58) Field of Classification Search
CPC ....... A61C 3/025; A61C 17/02; B24C 11/005; B24C 7/0023; B24C 5/04; B24C 7/0007; B05B 1/3426; B05B 1/3447; B05B 7/2462
USPC ................... 433/81, 88; 137/268; 604/82–85
See application file for complete search history.

(56) References Cited

U.S. PATENT DOCUMENTS

| 2,024,146 | A | * | 12/1935 | Crowther ........................ 424/49 |
| 3,386,439 | A | * | 6/1968 | Harper ............................ 604/84 |
| 3,566,863 | A | * | 3/1971 | Law et al. ..................... 601/160 |
| 4,540,365 | A | * | 9/1985 | Nelson et al. .................. 433/88 |
| 4,978,297 | A | * | 12/1990 | Vlock .............................. 433/88 |
| 5,395,323 | A | * | 3/1995 | Berglund ........................ 604/84 |
| 2004/0014001 | A1 | * | 1/2004 | Nordmo et al. ................ 433/88 |

FOREIGN PATENT DOCUMENTS

WO 2011070385 A1 6/2011

* cited by examiner

*Primary Examiner* — Heidi M Eide
(74) *Attorney, Agent, or Firm* — Hooker & Habib, P.C.

(57) ABSTRACT

A dental hygiene system includes a feed line for a liquid that engages and dissolves a dental cleansing compound before being discharged from a nozzle connected to the feed line and sprayed on the teeth for cleaning.

26 Claims, 9 Drawing Sheets

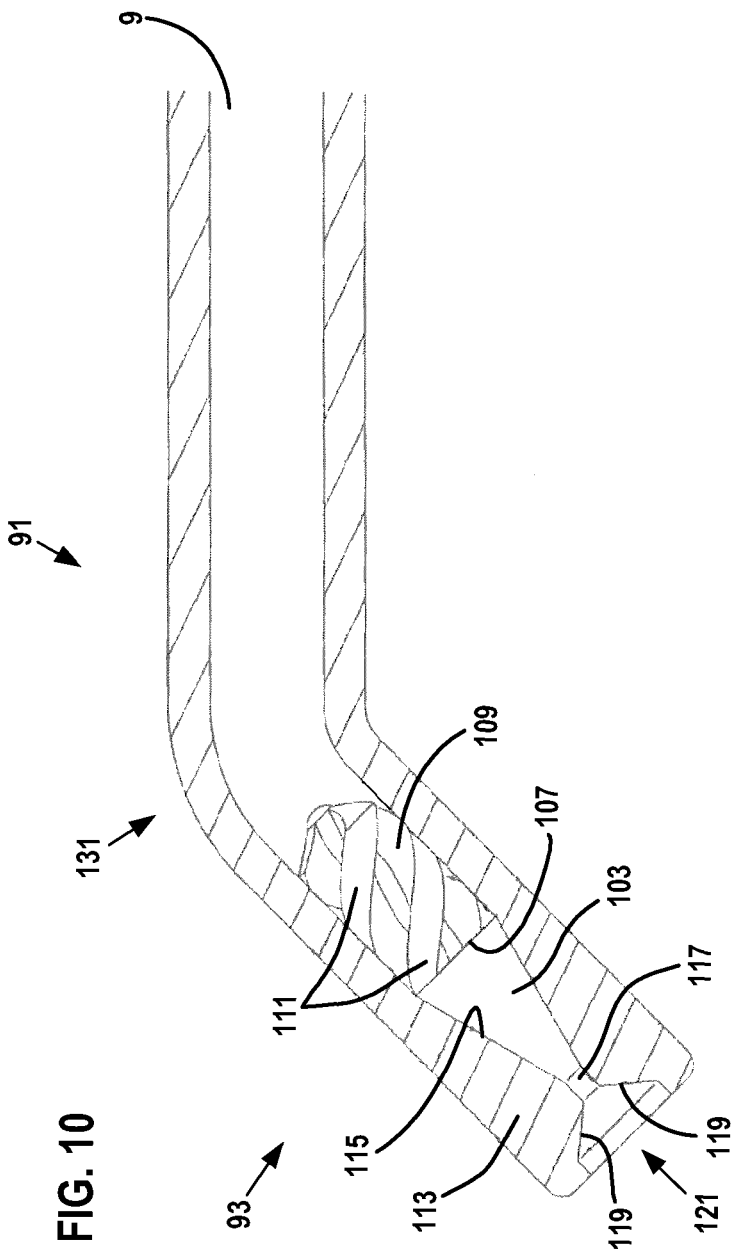

SYSTEM FOR DENTAL CLEANING

FIELD OF THE INVENTION

This invention involves in general the field of dental hygiene.

BACKGROUND OF THE INVENTION

Oral irrigators are well-known instruments of dental hygiene and serve to clean teeth, gums, and interdental spaces with a jet of a liquid. In general this is accomplished by shooting water, mouthwash, etc. under pressure through a nozzle.

Known also is the practice of adding materials to the stream of liquid which have an abrasive effect on the tooth surface when they encounter it.

The best available technology currently produces oral irrigators which are often complex to manufacture and complicated to use and to clean.

PURPOSE OF THE INVENTION

The purpose of this invention is to provide solutions for at least some of the problems afflicting existing oral irrigators.

BRIEF SUMMARY OF THE INVENTION

To achieve its purpose, this invention proposes a system for dental hygiene, a tooth cleansing compound, a receptacle to hold the cleansing compound, a device for dissolving the cleansing compound and mixing it with liquid to create a cleansing suspension and a nozzle for the discharge of the cleansing suspension in order to satisfy the independently existing expectations for the functioning of such a device.

The system of dental hygiene is comprised of a supply line, by means of which liquid is conveyed to the device; a dispersion chamber connected to this source of liquid which contains the cleansing compound and dissolves it in the liquid to create a cleansing solution; and a nozzle in fluid communication with this dispersion chamber to discharge the mixture of cleansing compound and liquid for the purpose of cleaning the teeth.

The cleansing compound is planned to be a multilayered tablet whereby each layer would consist of abrasive components consisting of magnesium oxide [MgO] and cross-linked polyvinyl pyrrolidone [PVP] together with other binders. The ratio of the abrasive components to the binders in the tablet varies such that the amount of magnesium oxide is greatest on the outside and becomes gradually less toward the inside while the amount of PVP is greatest on the inside and least on the outside—ideally in balanced proportions.

The receptacle for the cleansing compound consists of a chamber to contain the cleansing compound, at least one opening for the intake of liquids into this chamber, and at least one opening for the discharge of liquid and the dissolved components of the cleansing compound.

The dispersing device consists of a housing, a dispersing chamber in the housing, an intake for liquids into the chamber, a discharge for liquids out of the dispersing chamber and a receptacle in the chamber for the cleansing compound. This receptacle is at least semi-elastic in order that it may exert a preload force on the cleansing compound.

The cleaning nozzle is made of a semi-flexible material, in particular a semi-rigid plastic. It has a pressure chamber which is supplied with liquids via an intake line, a spinner located inside the pressure chamber, a nozzle discharge opening, and a compression area located between the pressure chamber and the nozzle discharge opening which becomes narrower as it reaches the nozzle discharge opening.

Additional preferred constructions may be found in the dependent claims, in the following description as well as in the attached drawings.

BRIEF DESCRIPTION OF THE DRAWINGS

The attached, schematic drawings illustrate various construction features of the invention which are then described in detail below. The drawings show:

FIG. 10 a cross-sectional view of a further possible design for a nozzle.

DETAILED DESCRIPTION OF THE DRAWINGS

Figure 1:
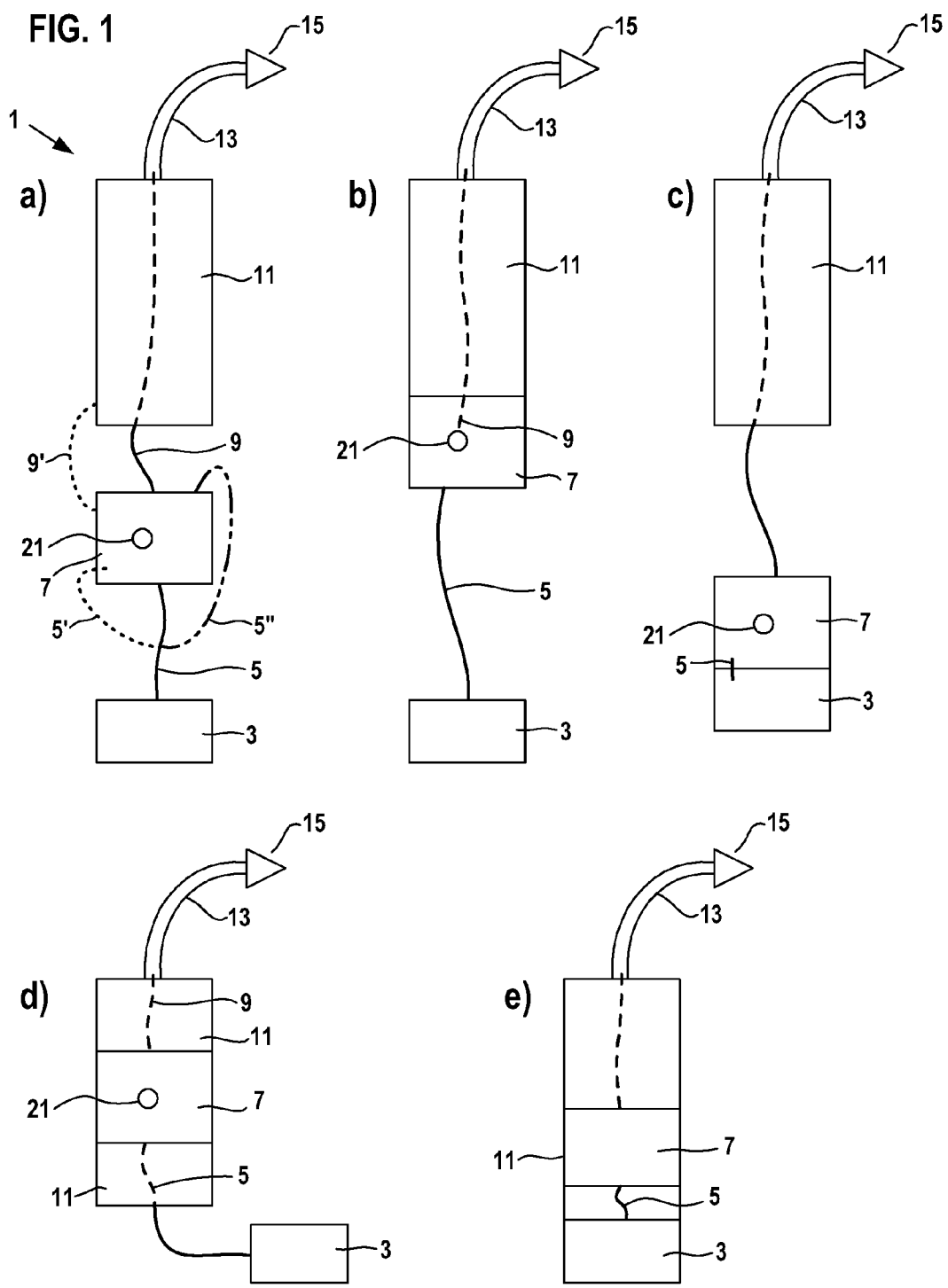
FIG. 1a-e schematic illustration of various components of an oral irrigation system.

The detailed description of the drawings are preceded by the following additional information regarding the invention.

Compared with powders, dental cleansing compounds in tablet form are easier to measure and use. Thanks to their compact structure they are easy to store and transport. Powdered components are mixed and pressed to produce the tablets.

One part of the invention involves the use of magnesium oxide [MgO] along with polyvinyl pyrrolidone [PVP] as abrasive elements in the dental cleansing compound. These abrasive elements are comparable in nature to dental enamel and for that reason can pose less of a risk of damaging the teeth. Biofilm and deposits on the teeth may thus largely be removed daily in a gentle and safe manner. In addition, these abrasive elements help bring about an even distribution of the dental cleansing compound in the stream of fluid. The need for other compounds now in use by other manufacturers of dental cleaners which promote dispersion but have no cleansing function may now at least be reduced. In this context and throughout this patent application, the term dispersion refers to the loosening of the abrasive elements in the dental cleansing compound matrix by means of a liquid and their subsequent incorporation into the fluid stream.

Magnesium oxide is approved for use as a food additive by the European Union and is suited for use in dental hygiene.

Cross-linked PVP [polyvinyl pyrrolidone] is a hygroscopic amorphous water-soluble powder. It is harmless to humans and promotes dispersion because of its swelling properties, but it also acts as an abrasive cleaning agent in the stream.

Because of its composition, the tablet manufactured according to this invention will hardly dissolve in water. A fluid stream is necessary to cause the components to disperse. For this reason a tablet remains effective for multiple uses and can remain in the device during pauses or periods of nonuse. In order to achieve an even volume discharge of abrasive materials, the outer layer of the tablet may have a higher proportion of MgO than does the core. In the outer layer the MgO will have immediate contact with the fluid stream designed to effect its dispersion; for this reason the proportion of those components which cause the tablet to break down upon contact with water may at least be reduced.

In the core layer, the cleansing compound mixture may contain 40% MgO and 50% PVP.

In the core layer, the cleansing compound mixture may contain 40%±1 MgO and 50%±1 PVP.

In the core layer, the cleansing compound mixture may contain 40%±2 MgO and 50%±2 PVP.

In the core layer, the cleansing compound mixture may contain 40%±3 MgO and 50%±3 PVP.

In the core layer, the cleansing compound mixture may contain 40%±4 MgO and 50%±4 PVP.

In the core layer, the cleansing compound mixture may contain 40%±5 MgO and 50%±5 PVP.

In the core layer, the cleansing compound mixture may contain 40%±6 MgO and 50%±6 PVP.

In the core layer, the cleansing compound mixture may contain 40%±7 MgO and 50%±7 PVP.

In the core layer, the cleansing compound mixture may contain 40%±8 MgO and 50%±8 PVP. In the core layer, the cleansing compound mixture may contain 40%±9 MgO and 50%±9 PVP.

In the core layer, the cleansing compound mixture may contain 40%±10 MgO and 50%±10 PVP.

In the outer layer, the cleansing compound mixture may contain 60% MgO and 30% PVP.

In the outer layer, the cleansing compound mixture may contain 60%±1 MgO and 30%±1 PVP.

In the outer layer, the cleansing compound mixture may contain 60%±2 MgO and 30%±2 PVP.

In the outer layer, the cleansing compound mixture may contain 60%±3 MgO and 30%±3 PVP.

In the outer layer, the cleansing compound mixture may contain 60%±4 MgO and 30%±4 PVP.

In the outer layer, the cleansing compound mixture may contain 60%±5 MgO and 30%±5 PVP.

In the outer layer, the cleansing compound mixture may contain 60%±6 MgO and 30%±6 PVP.

In the outer layer, the cleansing compound mixture may contain 60%±7 MgO and 30%±7 PVP.

In the outer layer, the cleansing compound mixture may contain 60%±8 MgO and 30%±8 PVP. In the outer layer, the cleansing compound mixture may contain 60%±9 MgO and 30%±9 PVP.

In the outer layer, the cleansing compound mixture may contain 60%±10 MgO and 30%±10 PVP.

There may be at least one intermediate layer of cleansing compound between the core layer and the outer layer.

In the intermediate layer, the cleansing compound mixture may contain 50% MgO and 40% PVP.

In the intermediate layer, the cleansing compound mixture may contain 50%±1 MgO and 40%±1 PVP.

In the intermediate layer, the cleansing compound mixture may contain 50%±2 MgO and 40%±2 PVP.

In the intermediate layer, the cleansing compound mixture may contain 50%±3 MgO and 40%±3 PVP.

In the intermediate layer, the cleansing compound mixture may contain 50%±4 MgO and 40%±4 PVP.

In the intermediate layer, the cleansing compound mixture may contain 50%±5 MgO and 40%±5 PVP.

In the intermediate layer, the cleansing compound mixture may contain 50%±6 MgO and 40%±6 PVP.

In the intermediate layer, the cleansing compound mixture may contain 50%±7 MgO and 40%±7 PVP. In the intermediate layer, the cleansing compound mixture may contain 50%±8 MgO and 40%+8 PVP.

In the intermediate layer, the cleansing compound mixture may contain 50%±9 MgO and 40%±9 PVP.

In the intermediate layer, the cleansing compound mixture may contain 50%±10 MgO and 40%±10 PVP.

The distribution of the components may vary discreetly from the outer layer's 60% MgO to the core layer's 30% PVP.

The remaining components in the layers may consist of binders and/or lubricants, for example magnesium stearate, and/or additives [e.g. fragrances and/or flavorings, medically effective substances].

The innermost layer may consist of ca. 40% MgO and ca. 50% PVP which will result in more rapid dispersion of a tablet reduced to its core; this is in order that the fluid stream may continue to contain the same amount of abrasive material as before.

The cleansing compound may have in each of the layers hydrophobic ingredients, particularly 1% highly dispersed silica, in order to improve its slip properties.

The cleansing compound may also contain additional medicinal, cosmetic or olfactory ingredients.

The receptacle for the tablet may be a woven material or a mesh, net or grid structure. Appropriate materials would include e.g. metal [e.g. wire], plastic [e.g. in thread or fiber form; e.g. nylon, thermoplastic resin, bio-plastic] or a combination of these. A stream of liquid such as water flowing around the tablet receptacle effects the dispersion of the abrasive components in the cleansing mixture contained within the tablet receptacle.

The intake and outflow openings can be so designed and/or constructed that the stream of liquid entering through the intake opening completely surrounds and flows around the cleansing compound. In addition, they may be so designed and/or constructed so that the stream of liquid first contacts predetermined areas of the cleansing compound [e.g. corner[s], edges, side surface[s].

The outflow opening[s] can permit a liquid with dispersed abrasive components to pass through. In addition, they may facilitate a homogeneous mixture of dispersed components in the fluid stream.

The outflow opening[s] can be so dimensioned that particle build-up or particles of a pre-determined size and larger will be kept inside the tablet receptacle. In this way clogging of tubes, nozzles, etc. further downstream can be prevented.

Residue can be further broken down by the stream of fluid and dispersed or simply removed with the tablet receptacle.

In addition, the tablet receptacle may consist of two parts that fit together.

At the same time the tablet receptacle may be disk shaped and so arranged that the cleansing compound is basically held at right angles to the fluid stream without rotating.

The parts of the tablet receptacle may be connected at connection areas to form a single interconnected unit. Possible means to effect this connection include welding, fusing, etc. The interconnected unit holding the tablet receptacle can be designed to be part of the dispersion chamber.

The cleansing compound can have a small space between itself and the inner surface of the tablet receptacle. Such a space or clearance between the cleansing compound and the tablet receptacle can help facilitate the dispersion of the cleansing components in the tablet e.g. when movement of the tablet causes mechanical abrasion. In addition this will guarantee that the fluid stream will flow around and contact the tablet basically on all sides. The space may have from close to $1/10^{th}$ to $1/20^{th}$ the diameter of the cleansing compound tablet.

The tablet receptacle can have inlet and outflow openings so designed to make possible the discharge of a homogeneous mixture of dispersed cleansing elements in the fluid stream.

The tablet receptacle may be disk shaped. Thus a flat tablet would be able to be exposed to the fluid stream without rotating.

The tablet receptacle may also have other shapes in order to accommodate a different tablet configuration or an alternative form of the cleansing compound. For example, the tablet receptacle may be designed as a pyramid, cube, or polyhedron.

In the dispersion chamber the fluid stream can flow around and contact the cleansing compound from all sides. In this way the fluid stream can produce vibration and movement in the cleansing compound. The interaction between the fluid stream and the cleansing compound will thus cause the latter to be dispersed in the former. In addition, one or more other structural elements [e.g. one or more holders or retainers] may cause the dispersion or additional abrasive components. The tablet receptacle or the dispersion chamber themselves may provide such structural components.

The at least semi-elastic nature of the dispersion chamber has the effect of maintaining the cleansing compound in the ideal position for optimum dispersion ["sweet spot"] even as its volume decreases. The center of gravity of the cleansing compound should be aligned relative to the fluid stream and be held in the in the middle of the stream.

In the dispersion chamber, the holder for the tablet receptacle may have at least two elastic fingers which are able to provide the cleansing compound with elastic pretensioning.

The fingers may have at least two elastic plastic holders to which the cleansing compound is attached. In doing so, the cleansing compound may be contained an a receptacle as described above.

The dispersion chamber may have a sieve-like structure. The pretensioning [e.g. by the fingers and/or tablet receptacle] can press the cleansing compound against the sieve. The sieve itself may be located by an outflow opening of the dispersion chamber.

The elastic pretensioning holds the cleansing compound tablet in the correct position even as the volume of the tablet deceases [e.g. by pressing it toward the sieve].

In this way it is possible to have the entire surface of the cleansing compound tablet continuously exposed to the flow of liquid and its flushing action. This provides for a constant, even and complete dispersion of the ingredients in the cleansing compound tablet into a specifically defined volume of fluid.

In addition, the elastic pretensioning permits the cleansing compound tablet to move around in the fluid stream. Where fingers are present, the force of the stream and possibly the out-gassing/swelling of the splitting agent PVP can transfer the cleansing compound to the fingers, where it will then move with them.

The location of the fluid inlet and/or the fluid outlet influences the stream of liquid inside the dispersion chamber. Thus it is possible for the dispersion chamber to have a linear flow path for liquid through the unit or to create turbulence in the flow of fluid.

So far as the dispersion chamber is concerned, the cleansing compound tablet may be contained within a receptacle manufactured according to this invention and suspended in an elastic holder inside the dispersion chamber. The pressure of liquid flowing into the dispersion chamber may lie between 4 bar and 10 bar.

The dispersion chamber may have a whirling element to create turbulence in the liquid being fed into it.

The whirling element creates turbulence or swirling of the liquid entering the dispersion chamber. The design of the fluid intake and/or the fluid outflow can enhance the effect of the whirling element. The whirling element may be designed as a cylinder and introduce fluid e.g. via angled holes into a swirl chamber. The whirling element can be constructed as an integral part of the holder. In order to accomplish this, the holder could have e.g. one or more passages or channels which would create the swirling action given the appropriate incoming flow.

The design of the disperser, particularly of the dispersion chamber may be such that the tablet will be continuously exposed to the fluid stream and substrate will be continuously dispersed even as the tablet is reduced in size by the dispersion of its outer layers. The diameter of the dispersion chamber may therefore be somewhat larger that the tablet so that it may easily be placed inside of the chamber. The length of the swirl chamber can be such that its volume will be kept at small as possible in order to keep the pressures as even as possible throughout the entire system.

Also included is the use of a dispersal system for the dispersion of a dental cleansing compound in the system for dental cleansing.

It is also possible for the dispersal system to have an upper and lower part that are connected to each other. The joining of the two parts may be accomplished by a snap or snap-in joint, a threaded joint, or some other appropriate mechanism.

The nozzle may be made of a semi-rigid plastic such as polymethylmethacrylate [PMMA] or hard polyvinyl chloride [unplasticized PVC]. Such semi-flexible materials are economical and easily substituted. The semi-flexible material inhibits the formation of blockages by abrasive particles because its malleable nature, particularly at the microscopic level, can permit an eigenvibration to take place in the nozzle when the stream of suspended components passes through it. This combined with the resonances caused by any periodic irregularities in the pressure of this fluid stream can inhibit the build-up of suspended particles and remove any short-term accretions. It will also work to reduce wear on the nozzle and guarantee sufficient strength to withstand initial pressures of between 4 and 10 bar.

In addition, the spinner assembly may have a conical, spiral-shaped or cylindrical design. The spinner assembly twists the liquid streaming through the nozzle and can force it into the compression zone. The spinner assembly may effect a twisting of the fluid stream which occurs immediately before the compression zone and makes possible a smoothly flowing current.

In addition, the inside walls of the compression zone may be smooth, for example coated. A circular widening of the nozzle opening or nozzle mouth may be between 30° and 60°, but optimally 45°, to the longitudinal axis of the nozzle at the discharge outlet.

The nozzle may be constructed as a hollow cone nozzle.

In the dental cleansing system, the cleansing compound may be housed in on of the receptacles described above.

The dental cleansing system may have a control element in which or to which the dispersion device may be attached.

The dental cleansing system may incorporate the source of the liquid or be connected to a separate source of the liquid.

Comparable elements in the diagrams carry the same reference numbers.

FIG. 1a-e illustrate various possible designs of a dental hygiene system [1].

The dental hygiene systems [1] include in each case a source of liquid [3], a feed line for the liquid [5], a dispersing device [7], a discharge line for the solution [9], a control device [11], and a nozzle attachment [13] with a nozzle [15].

The source of the liquid [3] may be a water tank with an integrated or attached pump system, or a direct hook-up to the domestic water line [spigot], in which case, however, a pump system placed before the dispersing device [7] would permit the creation of a pulsing fluid stream. The pump system may also be located upstream from the dispersing device [7]. From its source [3], the liquid is conducted through the feed line [5] to the dispersing device [7].

The design illustrated in FIG. 1a locates the dispersing device [7] between the control device [11] and the source of liquid [3] and between the two feed lines [5] and [9] which connect them. Thus it is e.g. possible to integrate the invention into a conventional dental cleaning system [oral irrigator] by inserting the dispersing device [7] between the source of liquid [3] and the control device [11].

In the design illustrated in FIG. 1b, the dispersing device [7] is linked to the control device [11]. The dispersing device [7] may be attached directly to one end of the control device [e.g. glued, fused, screwed, etc.] or be part of a single, one-piece unit. This variant could be used, for example, in dental hygiene systems in which the source of the liquid [3] (together with any pumping system which may be associated with it) consists of a separate tank in order that the handle containing the control device [11] might be as small as possible.

In the design illustrated in FIG. 1d, the dispersing device [7] is housed within the control device [11]. This variant may be used, for example, if, as shown in the diagram, the pump system and/or energy source is located at the bottom end of the control device.

In the design illustrated in FIG. 1c, the dispersing device [7] is linked to the source of liquid [3]. The dispersing device [7] may be attached directly to the source of liquid [e.g. glued, fused, screwed, etc.] or be part of a single, one-piece unit. A spigot fitted with an appropriate adapter may be used to attach the water source via a corresponding connector to the dispersing device [7]. This variant would also be appropriate for retrofitting an existing appliance.

FIG. 1e diagrams a design that incorporates all of the components listed above in a single integrated unit.

For all designs diagrammed in fig. 1a-1e, the supply of liquid may be carried out by means of one or several complementary or optional supply lines 5' and/or 5" long as shown in fig. 1a. The liquid supply entering at the side, as shown in the diagram, can affect additional swirl in the stream of fluid entering the device. An additional optional discharge line 9' may extend from the dispersing device [7] to the control device [11].

In the dispersing device, to be described in detail further below, it appropriate to use a dental cleansing compound, e.g. in tablet form [21] or as granules. The entering stream of liquid flows around the cleansing compound and washes most particularly the abrasive components out. The liquid mixes with these components to create a dental cleansing suspension.

In the case of all design diagrams 1a-1e, the outflow of the dental cleansing suspension out of the dispersing device [7] may occur through at least one supplementary or alternative outflow line, as shown in FIG. 1a.

The dental cleansing suspension is fed from the dispersing device [7]] through the control device [11] and the nozzle attachment [13] to the nozzle [15]. The nozzle attachment [13] either forms a single piece together with the control device or may be made to connect with it as a separate, interchangeable element. The dental cleansing suspension exits the device through the nozzle [15] to be available in the oral cavity for the purpose of cleaning the teeth.

Figure 2:
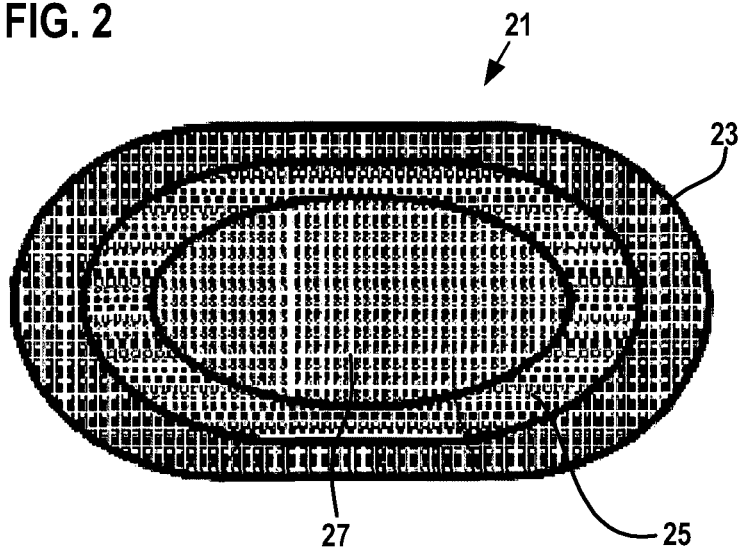
FIG. 2 a schematic illustration of one possible design for producing a dental cleansing compound in tablet form.

FIG. 2 illustrates a dental cleansing compound in tablet form [21]. The tablet [21] contains abrasive components that are present in several layers [23] and [25] and the core layer [27]. The tablet layers 23, 25, and 27 each contain the abrasive components magnesium oxide and cross-linked polyvinyl pyrrolidone (PVP).

PVP also inhibits the clumping or build-up of magnesium oxide components. PVP supports the dispersion or breaking down of the tablet [21] in the presence of the fluid stream. Since PVP swells in the fluid environment, it serves as a sort of "blasting agent" to help bring about a "controlled" breaking down of the tablet's structure.

The layers 23 and 25 and the core layer 27 which they enclose differ in the proportions of magnesium oxide and PVP which they contain as well as any binders or forming agents. Binders and forming agents, e.g. magnesium stearate, may be added. The binder may constitute ca. 5%-15% of the mixture. In addition, hydrophobic components such as dispersed silica may be pressed in to improve flowability.

The proportion of magnesium oxide and PVP changes from the outer layer [23] through the middle layer [25] to the core [27]. This it is possible to use 60% magnesium and 30% PVP in the outer layer [23]. The core [27] of the tablet [21] on the other hand may contain 40% magnesium oxide and 50% PVP. In the middle layer [25] there may be a ratio of e.g. 50% magnesium oxide to 40% PVP. In this way it is possible to achieve a quick and even dispersion of the tablet core [27] and thus also a constant concentration of abrasive components in the dental cleansing suspension.

Figure 3:
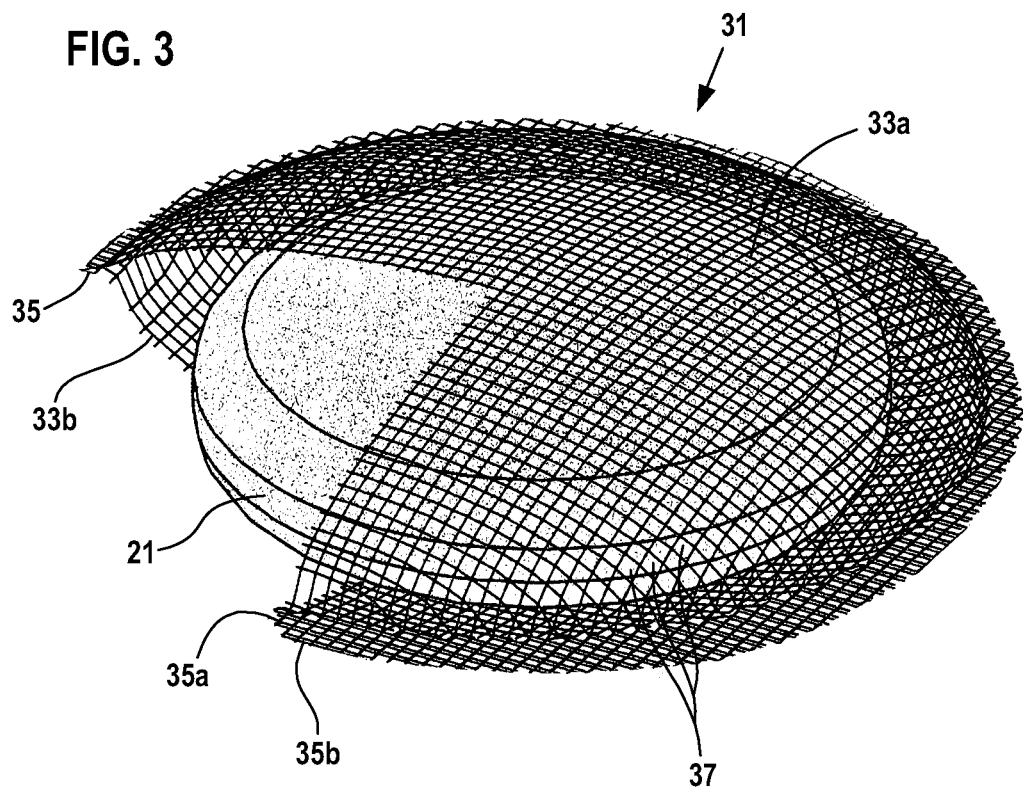
FIG. 3 a schematic illustration of one possible design for a receptacle for a dental cleansing compound in tablet form.

FIG. 3 illustrates an receptacle [31] for the insertion of a dental cleansing compound, e.g. a tablet or granular product. The receptacle [31] consists of an top part [33a] and a bottom part [33b], each of which is shell or disk shaped. The top [33a] and bottom [33b] parts are joined at their respective edges [35a and 35b]. The parts may be joined at the edges [35a and 35b] by a fused, pressed, or glued joint or by a click-stop or snap connection. The receptacle [31] may be made of plastic, metal, woven fabric, fiber glass, fleece, cloth fabric, etc. and well as blends of various materials. Whichever material is selected, care should be taken that the receptacle [31] be elastically deformable.

The receptacle [31] is designed for use in a dental cleansing system [1], particularly in a dispersion device [7]. The receptacle [31] has openings [37] through which liquid can enter and through which the dental cleansing suspension (see above) containing abrasive elements can exit. The openings [37] may be essentially of equal size, as the drawing in FIG. 3 illustrates. In the case of other designs, the openings [37] through which the liquid enters may be smaller than the opening [37] through which the dental cleansing suspension is intended to exit.

In the variant illustrated in the drawing, the openings [37] are provided by the grid-like, mesh, honeycomb or woven top and bottom parts or screens [33a & 33b]. Other variants could provide these screen openings [37] by means of punched or drilled holes, etc.

The openings [37] may be sized such that the suspension exiting the device may contain only abrasive elements of a particular size and smaller. In this way clumps or aggregations of dental cleansing compound may be prevented from exiting the device and clogging elements positioned downstream.

FIG. 3 illustrates a receptacle [31] in whose interior a tablet [21] has been positioned. The tablet is to be completely surrounded by the receptacle [31]. (In this drawing, a portion of the receptacle has been cut away for the sake of clarity.)

In the design variant illustrated here, the tablet [21] and/or the receptacle [31] are so sized that the tablet [21] has room to move inside the receptacle [31]. In this way an operative connection between the tablet and the inner surface of the receptacle may come into play which can lead to a mechanical wearing away of the tablet [21]. In addition, the ability of the tablet [21] to move inside the receptacle [31] makes it possible for fluid to contact it essentially from all sides.

The receptacle [31] makes it possible to hold the tablet [21] so positioned with regard to the flow of the liquid, so that for example a tablet placed crossways to the current will not be able to turn or realign itself to go with the current. In addition, the receptacle provides an (additional) swirl factor in the liquid stream intended to disperse the tablet [21]. This assists in dispersing the components in the tablet [21]. Following use, e.g. when the tablet [21] has been completely dispersed or essentially no more abrasive materials are present, the receptacle [31] may be removed and discarded. This action will also remove any tablet residue remaining inside the receptacle.

Figure 4:
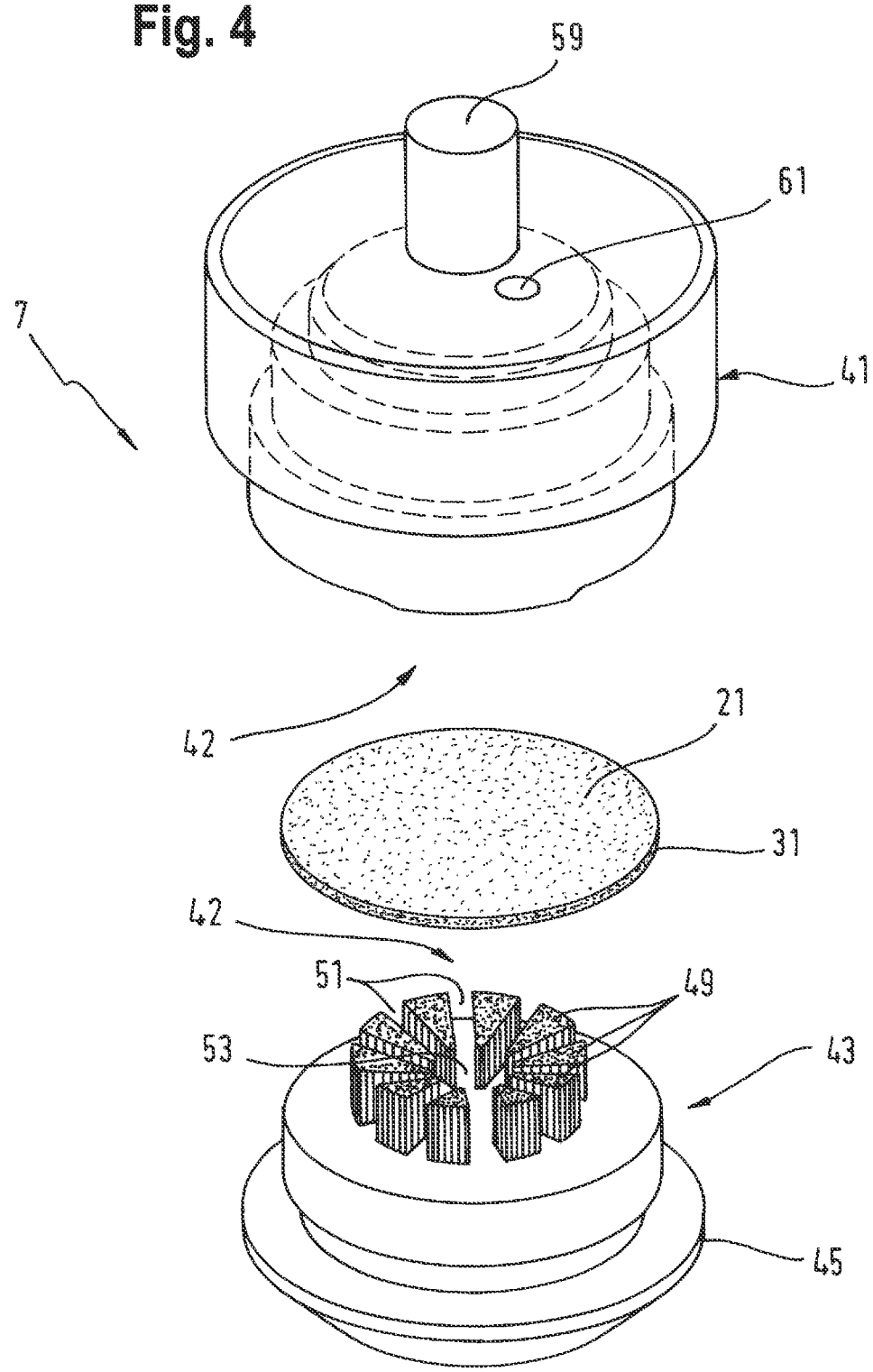
FIG. 4 a perspective, exploded view of one possible design for the construction of a dispersing chamber.

FIG. 4 illustrates a design for a dispersing device [7] for a dental hygiene system [1] as described above.

The dispersing device [7] consists of a dispersing chamber [42], which in the variant shown takes the form of a cylinder by way of example, and is intended to accept a dental cleansing compound. FIG. 4 illustrates a dental cleansing compound in tablet form [21] by way of example. The dimensions of the dispersing chamber [42] here are such that the dental cleansing compound is exposed on all sides to the stream of liquid and dispersed from all sides into it.

The dispersing device [7] consists of an upper part [41] and a lower part [43] with a base [45]. On the base [45] is located a holder which has pedestal-like holding members or supports. They holding members [49] may be at least semi-elastic (e.g. in the upper portion shown in the diagram). The supports [49] are separated from each other by spaces [51] and there is as well an open space in the center [53]. As shown in the diagram, the upper part of the supports [49] is higher on the outside than on the inside. This creates a cone-shaped support for the dental cleansing compound.

The holding members [49] are designed to accept and/or store a dental cleansing compound (e.g. in the form of a tablet [21] or in a receptacle [31]. Any elasticity present in the holder or its supports [49] and/or the elasticity of the receptacle (if present) provide(s) for an elastic pretensioning which affects the dental cleansing compound positioned between the holder and an opposing counter surface present in the upper part of the dispersing device [41].

Liquid is supplied to the dispersing chamber [42] by means of an intake line for liquids (e.g. the intake line 5) from FIG. 1. The may enter the device from the bottom, as illustrated in the drawing, in order to create a stream of fluid vertically through the spaces 51 and 53. Supplementary or alternatively, liquid may also be introduced (e.g. laterally) so that a fluid stream results which exhibits at least in part a radial and/or longitudinal flow pattern and consequently a turbulent or swirling action through the circular cross-section of the dispersing chamber. This flow-through is maintained so that the tablet is continuously and evenly exposed to the liquid on all sides.

Further, on the upper part [41] is found a fastener [59] which is intended to attach to a control device [11] of a dental hygiene system. The control device [11] may have, for example, a corresponding socket to receive the fastener [59] and attach to it by a threaded coupling or be otherwise fused or glued in place. In addition, an outlet [61] has been provided on the upper part in order that the liquid suspension may exit the dispersing chamber [42].

During operation, liquid is introduced into the dispersing chamber [42] and may be then swirled or given a rotating movement. The stream of fluid in the dispersing chamber interacts with the dental cleansing compound so that the latter is progressively washed away and a suspension of the dental cleansing compound in the liquid is created. This suspension is then drawn off through the outlet [61] and used to clean the teeth.

Figure 5:
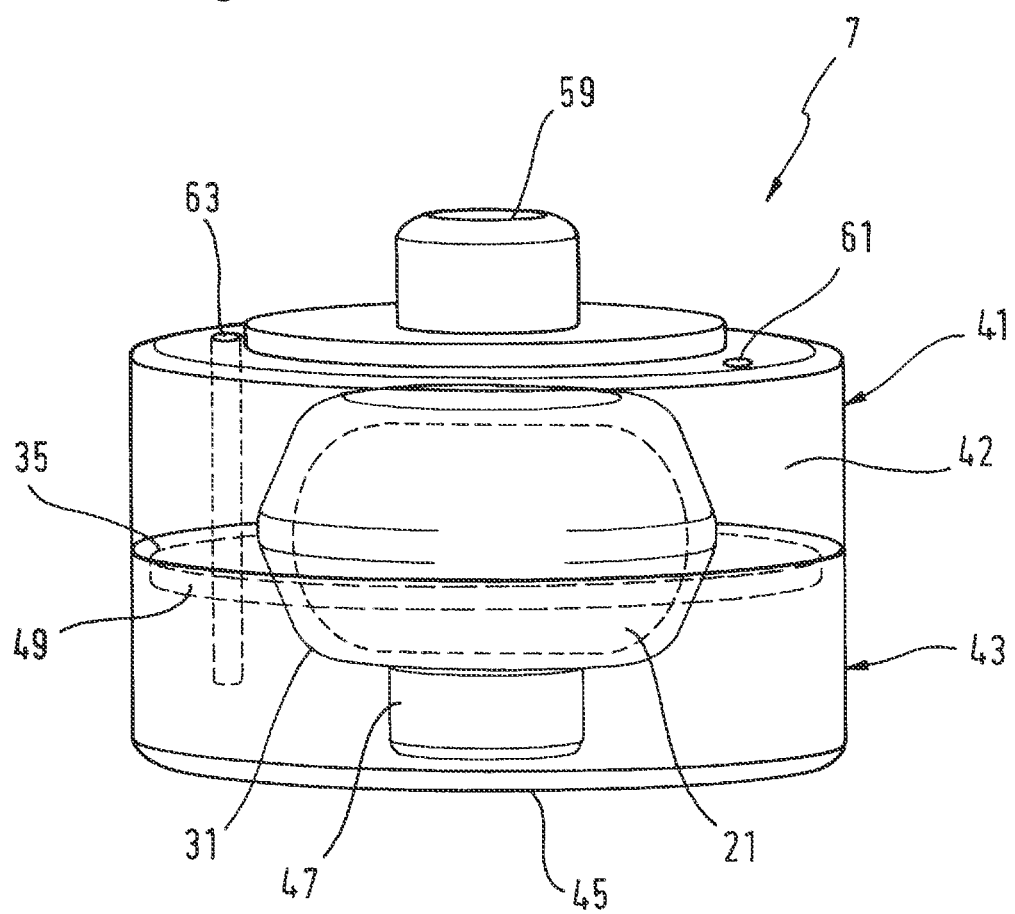
FIG. 5 a perspective view of another possible design for the construction of a dispersing chamber.

FIG. 5 gives a perspective view of a different design of a dispersing device [7] with a dispersing chamber [42]. The dispersing chamber [42] consists of an upper [41] and a lower part [43] with a base [45]. These parts may be joined with one another e.g. by means of a threaded connection or a click or snap closure. By means of a feed line [5], liquid is introduced through the upper part [41] and conducted to an inlet area in the lower part [43], as shown in the diagram. Inside the dispersing chamber [42] is intended to be a dental cleansing compound in the form of a tablet [21] enclosed in a receptacle [31].

The receptacle [31] is kept in position in the dispersing chamber [42] by a holder. In this case the rim [35] of the receptacle [31] rests on a holding member formed as a ledge [49] that runs around the inner wall of the dispersion chamber [42]. In addition, the bottom of the receptacle's lower portion [33b] rests on an optional pedestal-like support [47] and thus receives support from below. The receptacle's upper part [33a] is further supported by the inside surface of the upper part of the chamber [41].

The holder, together with the support structure [47], if applicable, insures the positioning of the receptacle [31] inside the dispersing chamber [42]. As an optional addition, the top side of the receptacle [31] may support itself against the inside of the upper part of the dispersing chamber. The elastic receptacle keeps the dental cleansing compound under tension.

In the upper part [41] there is an outlet [61] through which the liquid suspension may be channeled away from the dispersing chamber [42].

When in use, liquid is introduced through the inlet [63] into the dispersing chamber [42]. There it flows around the dental cleansing compound or tablet [21] which is contained within the receptacle [31]. The liquid becomes turbulent and experiences rotational forces. The turbulence and swirling or rotation of the liquid may be enhanced by means of an appropriate coating, e.g. teflon, on the inside surface of the dispersion chamber [7]. Also possible would be surface geometries on the inside of the chamber that would strengthen the turbulence and/or swirling of the inflowing liquid, e.g. a spiral or snail-like configuration of the walls or through the presence of paddles or vanes inside the chamber.

Particles of the dental cleansing compound of a particular size leave the receptacle [31] together with the liquid and enter the surrounding dispersing chamber [42]. The dental cleansing suspension exits through the outflow [61] and is available for cleaning the teeth.

Figure 6:
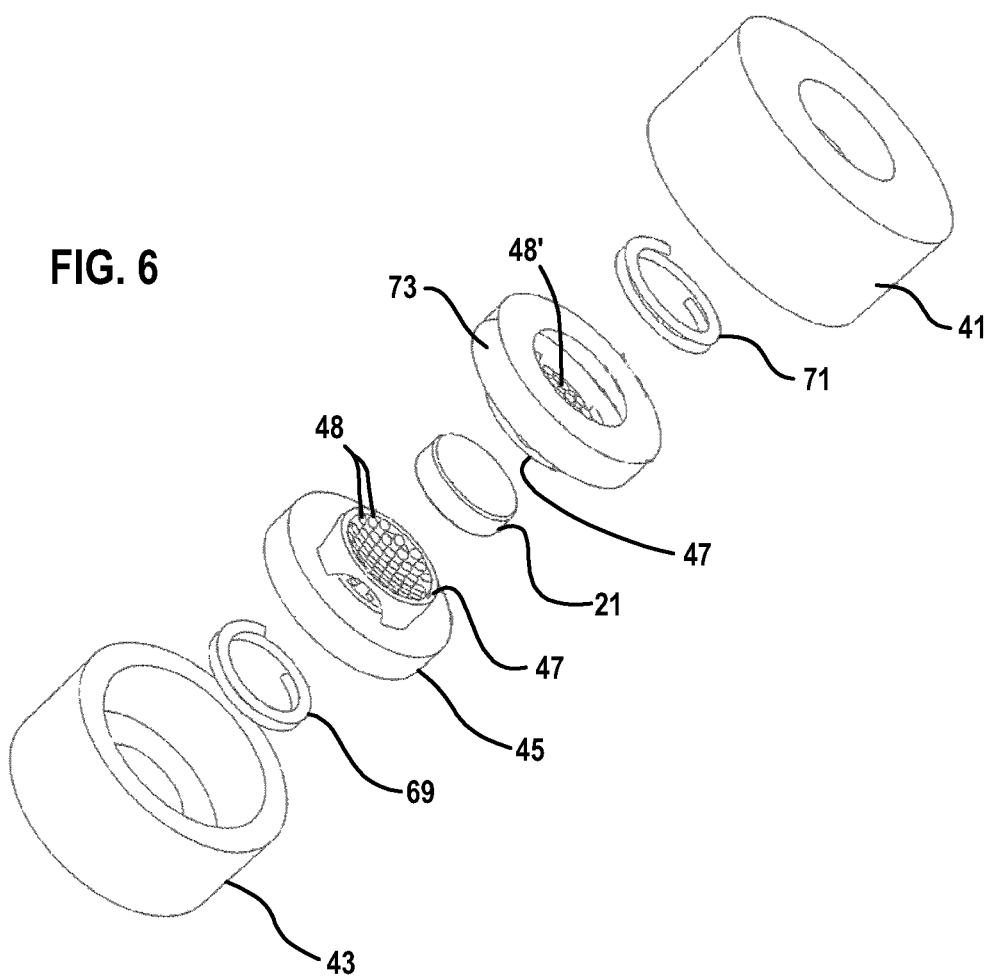
FIG. 6 a perspective, exploded view of another possible design for the construction o a dispersing chamber.

FIG. 6 shows a schematic exploded view of a further design for a dispersion device [7]. A housing with an upper [41] and lower part [43] contains a holder which will be described in detail below. A base [45] inserted into the lower part [43] and shows a support structure [47] for a dental cleansing compound to be placed on it. The support structure [47] has openings or orifices [48] built into it.

The counter-surface [73] has openings [48'] to permit liquid to flow through. In use, a dental cleansing compound is placed between the support structure [47] and the counter-surface [73].

A spring is provided between the upper part [41] and the counter-surface [73]. A second spring is located between the base [45] and the lower part [43]. The two springs [69 & 71] provide for the elastic pre-tensioned positioning of the dental cleansing compound.

Figure 7:
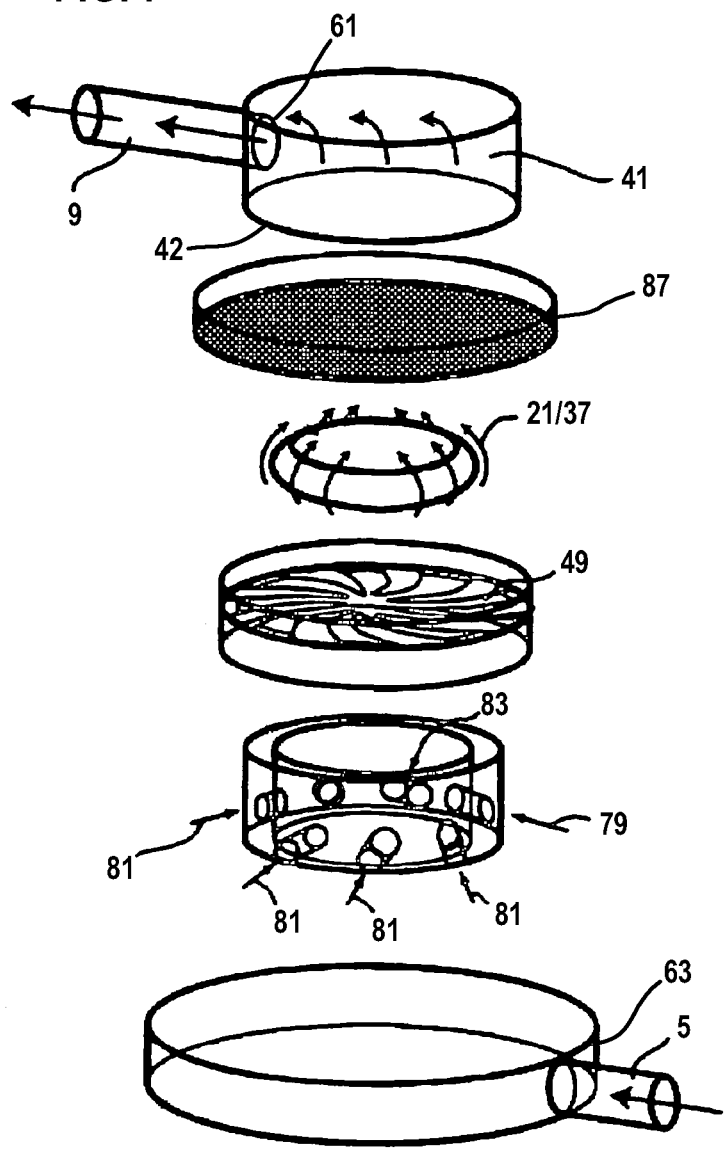
FIG. 7 a perspective, exploded view of another possible design for the construction of a dispersing chamber.

FIG. 7 shows a schematic exploded view of a further design for a dispersing device [7] with an upper [41] and a lower part [43].

Here a cavitation device [79] is intended to be part of the dispersion chamber. The cavitation device [79] is circular, or better cylindrical in shape and has slanting openings or through-holes [81] in the side walls through which liquid flows into a swirl chamber [83] inside the cavitation device [79]. The slanted inlet holes [81] create additional swirl.

A holder is attached above the cavitation device [79] which has inward reaching (spiral) supporting arms [49]. The supporting arms [49] may be made of an elastic, malleable and springy material, e.g. plastic, fiber glass etc. The supporting arms [49] serve to hold and position a dental cleansing compound (e.g. in the form of a tablet [21] or contained in a receptacle [31].

Above the dental cleansing compound a grid or sieve-like structure [87] is planned. The support arms [49] will press the dental cleansing compound against this structure.

The design includes an outflow [61] through which the cleansing suspension may be conducted out of the dispersion chamber by means of a discharge line [9].

When assembled, the cavitation device or swirl element [79] is located inside the lower part [43]. The holder is either placed on top of or located inside of the cavitation device [79]. The supporting arms [49] then press the dental cleansing compound against the sieve-like structure [87] to supply the pre-tensioned positioning of the dental cleansing compound. This effect may be enhanced if the sieve-like structure is designed to have elastic properties.

When the unit is in operation, liquid flows into the dispersion device [7] through an inlet [63] in the lower part [43] and into the cavitation chamber where it experiences rotation and swirling. The liquid then flows through the through-holes [81] in the swirl chamber [83] located inside the cavitation device [79]. From there, the swirling liquid flows through the supporting arms [49] and flows or washes around the dental cleansing compound. This action causes the dental cleansing compound [21] to begin to break apart and the loosened particles, most particularly the abrasive components, are carried by the stream of fluid through the sieve-like structure [87] and then out through the discharge opening [61].

The sieve-like structure [87] may be made to be an integrated element in the upper part or alternatively designed to be removable from the upper part.

Figure 8:
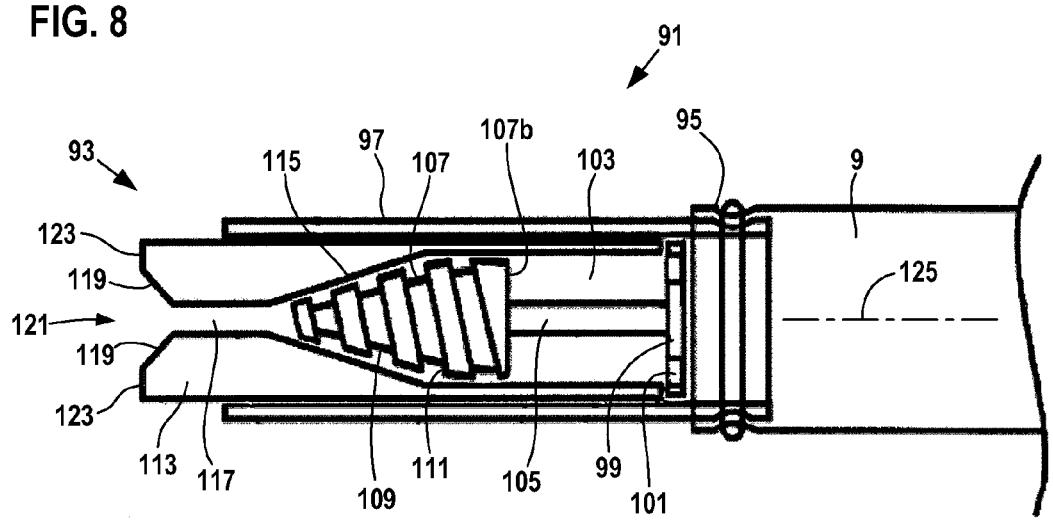
FIG. 8 a cross-sectional view of one possible design for a nozzle.

FIG. 8 shows a cross-section of a nozzle [91] designed to effect the jet blasting of the dental cleansing compound. The nozzle [91] is attached on one end to a feed line [9] by means of a connector [95]. The connector [95] may be designed as a mounting ring or clip collar which the presses the feed line [9] against the nozzle [91].

The nozzle [91] consists of a nozzle unit [93] which is contained in a sleeve [97]. The sleeve [97] and the nozzle unit [93] are joined to one another, e.g. glued, fused, etc. Alternatively, they may be designed and fabricated as a single piece.

A filtration device [99] is attached to the end of the nozzle unit [93] where it joins the feed line [9]. The filtration device consists of openings, e.g. drilled holes or grooves [101]. Downstream from the filtration device [99] lies a pressure chamber [103]. Inside the pressure chamber [103] a connecter [105] extends along the longitudinal axis of the nozzle [125] which is either connected to the filter [99] or formed together with it as a single piece. At the opposite end of the connector [105] is a spinner head having the form of a spinner means [107]. The spinner means [107] tapers down conically in the direction of the flow. On the surface of the spinner means [107] there are helical or spiral grooves [109] alternating with raised ridges [111]. The grooves [109] and ridges [111] impart spin to the fluid stream as it passes through the nozzle [91].

As the fluid enters, it flows first through the pressure chamber [103] and then hits the flat end [107b] of the spinner means [107]. As this occurs, the fluid is diverted to flow around the outside edges of the spinner means [107].

The nozzle unit [93] incorporates a housing [113]. The housing [113] surrounds an essentially uniform ("linear") space, which defines the pressure chamber [103] and surrounds part of the spinner means [107]. Downstream from this point, the housing [113] tapers down to form a discharge channel [117]. Thus a compression zone is created between the spinner means [107] and the tapering walls [115] of the housing [113]

After the tapering down [115] the discharge canal [117] continues in the direction of the flow to the mouth of the nozzle [121]. After this point, the mouth of the nozzle or discharge outlet widens like a funnel toward the exit. The degree of slope in this case may be at 45° to the longitudinal axis [125]. Thus the mouth of the nozzle is designed as a sort of discharge funnel. After the funnel surfaces [119] the mouth of the nozzle again flattens out, approximately at a 90° angle to the longitudinal axis [125], to create the end surfaces [123].

The liquid or suspension flowing around the spinner means [107] is given spin and accelerated in the process of which the exit pressure of the stream is also increased. The channel [117] serves to create further pressure and spin on the fluid stream. In this fashion it is possible to achieve exit pressures of between ca. 4-11 bar. The funnel-shaped opening [119] produces a exit spray in the shape of a hollow cone, which has the effect of lessening the pressure. The flattened ends [123] assist in maintaining an exit flow concentric to the nozzle's longitudinal axis [125].

Figure 9:
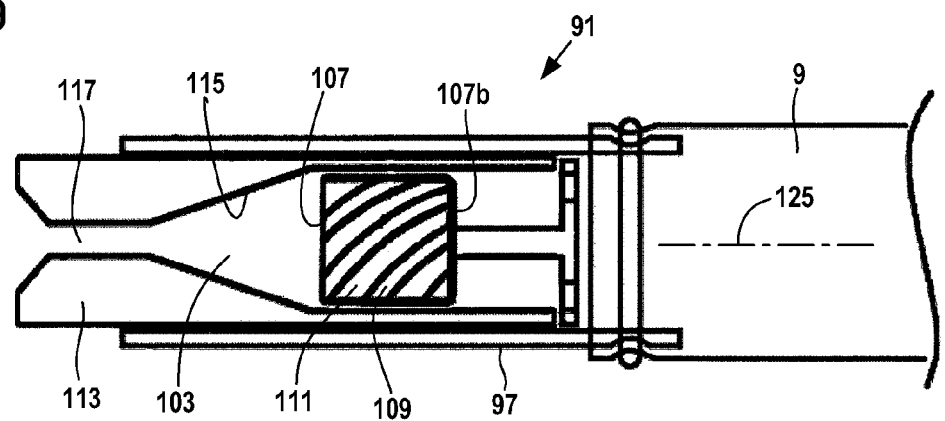
FIG. 9 a cross-sectional view of another possible design for a nozzle.

FIG. 9 illustrates a further design of a nozzle [91]. This variant is essentially the same as the design in FIG. 8. The spinner means is envisaged as an essentially cylindrical shape [107]. FIG. 10 shows a cross-section view of a further design for a nozzle [91]. A feed line for liquids [9] is integrated into a nozzle housing which is connected to a nozzle assembly [93].

The end of the nozzle assembly [93] that has the nozzle opening or nozzle mouth [121] displays a curved bend or angle [131] at approximately the one third point of its entire length. The angle [131] may be at ca. 45°-60° to the longitudinal axis [125]. This results in an optimal placement of the nozzle mouth [121] and permits a more ergonomic manipulation of the device when used to clean the teeth. The curve [131] interferes insignificantly with the dispersal pattern in comparison with the straight-line nozzle. In the oral cavity it enables the user to clean even difficult to reach spots on the teeth. In addition, the bend [131] imparts a tangential lead-in to the fluid stream as it engages a spinner means [107]. This creates additional rotation in the fluid stream.

The spinner means [107] is located directly in a cylindrical section of the tube and the smaller volume of the tube reduces the total area available for nozzle openings (nozzle lumen) with a corresponding increase in pressure on the fluid stream. The spinner means [107] is made funnel-shaped on its end in order to increase the velocity of the fluid stream. The abrasive particles present in the suspension are thus given additional kinetic energy and acceleration. The eigen-vibration or oscillation of the nozzle [91] prevent the build-up of abrasive and insoluble materials and particles in the suspension and thus particularly clumping or build-up resulting from eddies or dead zones. Normally there is no clogging of the nozzle [91], particularly where PMMA and hard PVC are used in its construction.

The spinner means [107] also displays grooves [109] and raised ridges [111], which in this case are designed as ridges and flutes symmetrically arranged and offset by 120°. After flowing around or passing the spinner means [107] the fluid stream enters the funnel-shaped, tapering pressure chamber [103]. The funnel-shaped pressure chamber [103] empties at its outlet into a linear discharge channel [117] or small diameter. The diameter may be e.g. 0.6 mm. The nozzle opening or the nozzle mouth consists again of a discharge funnel of opposite orientation which widens into funnel-shaped opening. The fluid stream has an initial pressure of between 4 and 10 bar in the feed line, approximately the same as the primary pressure ahead of the nozzle.

The nozzle [91] may be designed as a hollow cone nozzle. Such a design is particularly resistant to clogging. In addition, this design creates a highly dynamic fluid stream. A hollow cone nozzle reduces water consumption in comparison with a full cone nozzle or a solid stream nozzle. In addition, the jet of liquid from a hollow cone nozzle is more powerful around the edges and thus increases the cleansing effect in comparison with a concentrated stream.

The following remarks describe additional aspects of the invention, they do not purport to offer preferable options, however.

The invention also involves a dissolvable tablet with abrasive components. For various applications involving cleaning devices which employ a stream of water to cleanse an object, there is an advantage to using cleansing tablets that dissolve in the wash water or water jet.

Cleansing agents in tablet form enjoy a number of advantages when compared with such agents in powder form: They are easier to measure out and use and have the advantage as well as the result of their compact form when it comes to storage and transport. The production of the tablets generally involves mixing the ingredients in powder form and then pressing them into tablets or using them as granules.

One problem which regularly occurs whenever tablets are used is the length of time they take to decompose and dissolve which prevents the active ingredients from becoming active in the cleansing medium quickly enough. One significant reason for this problem originates in the manufacture: the production of sufficiently break-resistant tablets requires pressing at such high pressures that over-compaction of the tablet results.

The technology currently available has described various attempts to improve the solubility. These are frequently cumbersome, time-consuming and expensive. Various blasting agents and splitting agents are also well known.

At the same time, it is possible to describe tablet degrading agents which increase the speed with which tablets dissolve in the cleansing medium. Polymeric degrading agents for this application include polymers that swell up on contact with water as well as such that facilitate the inflow and/or outflow of water by creating channels in the tablets of cleanser. Polymer degrading agents for such applications include starches and cellulose and their derivatives, alginate, sugar, polyvinyl pyrrolidone, et al.

One disadvantage of known processes involving the use of blasting agents has to do with the often insufficient dissolution of these tablets when there is only a limited volume of water available for flushing. In this case it is either so, that when the volume of water is exactly what is required to dissolve the tablet completely, the concentration of the flushed-out ingredients sinks significantly toward the end, or if the volume of water is measured such that the concentration of the ingredients remains relatively constant, an undissolved remnant of the tablet generally remains.

The development and production of stable multi-layered tablets is time consuming and expensive and often overly sensitive to fluctuations of internal and external parameters in the process.

Neither is an even release of abrasive blasting agents guaranteed, since they are not intended to dissolve in water. Their residues frequently lead to the clogging of blast nozzles when the loss of chemical binding agents other additives releases clumps of granulate.

The invention should therefore present a collection of such flushable tablets which effect a more even dissolution, avoid substances not relevant to the task of cleaning, and do not cause undissolved residues to remain in the dispersion chamber and downstream piping, tubes, and nozzles.

This will be accomplished in terms of the invention by using a combination of magnesium oxide as an abrasive blasting agent together with cross-linked PVP. The first of these forms colorless crystals in the sodium chloride structure and is prepared through thermal reaction with other magnesium compounds. It is often used in the construction and food industry, e.g. as an acidity regulator or as a release agent. In addition it is approved as a food additive with the designation E 530 without limit (quantum satis), and is thus particularly suited for dental care in contrast with some of the aforementioned ingredients.

Admittedly magnesium oxide does tend to clumping when present a high concentrations in water, and these clumps can clog the nozzles of blasting devices. For that reason the use of caustic calcined magnesite, which is prepared by calcinating naturally occurring magnesium carbonate (magnesite) and which is especially susceptible to such clumping. Nevertheless, MgO may only be employed as an abrasive in limited quantities if the goal is a constant and complete dissolution of the tablets.

In addition to MgO, the invention makes use of one further blasting agent which may serve concurrently as a splitting agent to bring about the controlled breaking down of a structure under the influence of water. This was found following extensive trials in PVP which finds use for a number of reasons in tablets. Simple PVP ("linear" polyvinyl pyrrolidone) is a hygroscopic, amorphous powder, which quickly dissolves in water. And while the starting ingredient, polyvinyl pyrrolidone, is regarded as a category 3 carcinogenic, the cross-linked polymer is considered harmless to humans and is even often used in pharmaceutical applications (it is listed in EN AB 6.0 under the name crospovidone).

For that reason and because of its swelling properties, the cross-linked variant is suited for use for the targeted disintegration of form pressed tablets and also as a further, gentle abrasive blasting agent. In this regard it proved to be advantageous in seeking to achieve a constant release of abrasive components to have a higher concentration of MgO on the outer layer of the tablet, where the flushing of these components occurs readily without the assistance of disintegrating substances. To achieve this, it is sufficient, however, simply to introduce the materials stepwise into the press form in order to avoid a complicated manufacturing process.

The distribution is therefore gradual from the outer layer having 60% MgO and 30% PVP while the remaining 10% of the components would be binders and forming agents, e.g. magnesium stearate and other additives appropriate for the particular intended use. In contrast, the core of the tablet should contain only 40% MgO and 50% PVP which should lead to a quicker disintegration of the remainder of the tablet and a constant release of abrasive elements—in relation to the volume of water used in the flushing—which should prevent clogging.

In addition, it is possible to improve the flow characteristics of the mixture by including hydrophobic ingredients, e.g. highly dispersive silica.

According to the invention, the flushable tablet with abrasive components may consist of a mixture of magnesium oxide and cross-linked polyvinyl pyrrolidone (PVP).

According to the invention, the flushable tablet with abrasive components may have different layers with different proportions of the components in those layers.

According to the invention, the core of the flushable tablet may have abrasive components in the ratio of only 40% MgO and 50% PVP.

According to the invention, outer layer of the flushable tablet with abrasive components may contain 60% MgO and 30% PVP.

According to the invention, the flushable tablet with abrasive components may contain hydrophobic ingredients, e.g. 1% highly dispersive silica, to improve the flow characteristics of the other components.

According to the invention, the flushable tablet with abrasive components may contain additional medicinal, cosmetic or olfactory ingredients.

The build-up of a tablet begins with a core, which consists of 50% PVP and 40% of stronger abrasive MgO particles, a transition layer with a ratio of 50% MgO and 40% PVP and an outer layer, which is made up of 60% MgO and only 30% PVP.

The invention also involves a system for the dispersal of a tablet or of a granulate in a stream of water, specifically a water jet system, in which media, which contain abrasive, or scouring or polishing components, are contained in or surrounded by a so-called "mesh", a receptacle, e.g. of fabric, or a metal or plastic mesh, net, or fiber grid, for the purpose of promoting a constant disintegration and in order to prevent or inhibit accumulations or aggregations of tablet constituents which could clog filters or nozzles.

Depending on the purpose, tablets, a powder or a granulate will be used to introduce into a jet or stream of water ingredients or components for the purpose of cleaning or gardening or processing something. Typically dispersing devices will be used to hold the tablets or the powder, through which a stream of water will be conducted, which will cause the media to disintegrate in a gradual and constant fashion and which will then conduct the resulting suspension to a spray nozzle or the like.

Most such systems have various disadvantages, however. The disintegration normally tends to be rather uneven. At the mercy of a particular flow path and especially of currents that are difficult to anticipate or predict, the tablets disintegrate unevenly on the outside and powder or powder residue collect at the various dead zones of the dispersing device. This requires that an excessive volume of water be injected to effect a complete disintegration which in turn leads to periodic decline in the concentration of substances or materials in the suspension. In addition, the chamber must be cleaned after use, which in its own right constitutes an unpleasant chore.

Partly dissolved components tend to coagulate and may clog filters and nozzles or openings or apertures. This requires careful selection of the materials to be assembled and often inhibits the most advantageous concentration of a particular substance.

Most particularly it is the abrasive media—they tend in any case to be the most compact elements in any blend of ingredients—which build up or collect and clog the peripheral areas or edges of constrictions as the result of their greater mass and consequently stronger centrifugal momentum in turbulent situations and as a result of their more coarse-grained surface.

Existing technology provides various suggestions for the way in which media, especially abrasive media, should be selected and mixed for use in a stream of water. In most cases this involves injecting them into the stream of water using gas under pressure or injecting them into the dispersing device.

These various suggestions often result in manufacturing processes which are expensive, difficult to manage and have often the disadvantage, that deposits collect in dead zones and behind constrictions.

Research into the use of abrasive media for dental cleansing revealed that enclosing or placing the tablet or powder in a "mesh" (a receptacle) of appropriate dimensions could resolve the above named issues.

First it was discovered that the receptacle should provide for a system of slight but evenly distributed turbulence or swirling in the stream of water surrounding it, so that the disintegration of the substance might also proceed evenly as long as there would be adequate space or separation between the receptacle and the surface of the tablet or powder. Optimally this separation should be $\frac{1}{10}$ the thickness of the tablet or surface of the powder.

This derives from the close relationship between particle size of a particular abrasive medium, the distance and the size of the receptacle or of the fabric, grid, net, or mesh. A receptacle having a fabric, grid, net, or mesh with openings of ca. 0.3 mm provides for good disintegration if the size of the particles is between ca. 4 and 6 mil, the tablet has a diameter of ca. 30 mm and a thickness of ca. 6 mm, and the distance between the receptacle and the upper side of the tablet is approximately 3.0 mm.

In addition, the gaps in the receptacle permit small particles of the abrasive media simply to pass through while larger aggregations of particles will not be able to reach the stream of watery suspension. It then followed that deposits or material residues, such as cohering abrasive particles, would be able to be retained inside this structure and simply disposed of together with the tablet receptacle after use.

The invention involves a tablet or granules containing abrasive media which are contained in or surrounded by a flexible but sufficiently sturdy receptacle which is exposed to a stream of water which would dissolve soluble components and flush released abrasive particles into a stream of watery or fluid suspension whereby any residues absolutely resistant to disintegration would remain within the receptacle and may be disposed of with it.

The disintegration functions especially well so long as the receptacle is kept at a certain distance from the compacted tablet or tablets or when granulate is sufficiently loose inside the receptacle.

A disk-like receptacle has proven to be the optimal configuration in which a tablet may be exposed to a vertical stream of water without being able to turn sideways in the stream or otherwise align itself with the flow.

For that reason with regard to an uncomplicated manufacturing process the preferred design of this invention is a disk-like receptacle which consists of a two ply or double layered structure with a tablet or a small amount of granulate located between the layers which are joined or fused around the edges to create a rim a few millimeters wide which may be used for mounting purposes.

The continuous supply or delivery of abrasive components or ingredients results in a flow of suspension or stream in which agglomerations of particles or combinations of the same do not exceed 0.3 mm in size. This remains essentially constant during the entire disintegration process as long as sufficient abrasive particles are present inside of the receptacle. Any re-conglomeration, re-compounding or re-combination of ingredients that might occur will remain inside the receptacle and tend to resolve into the stream before they can clog filters or openings. This contributes to the delivery of an essentially constant concentration of media present in the stream of water. This is particularly the case toward the end of the process when only a small amount of the substance remains. This remnant then typically creates a cloud of media in the receptacle which is then carried away in relatively abrupt fashion.

The stream of suspension which emerges from this receptacle will pass through curved nozzles (30° of curvature at the nozzle end) without clogging them as a result of the constant flow pattern of the suspension.

Residues which cannot be dissolved and adhering accumulations or agglomerations do not need to be removed by scraping them out of the receptacle because they may be removed easily by simply opening and shaking the unit to permit the receptacle containing all the residue to fall out.

A tablet contains abrasive particles and is, according to the invention, encased or enclosed within a receptacle consisting of two disks or plate-like basins which are joined together by a bond, in particular by fusing the rims or edges of the two parts together.

With regard to the system of dissolving a tablet or granulate in a stream of water, the tablet or granulate may be completely contained or enclosed in a flexible but adequately sturdy receptacle or woven grid, mesh structure or net.

According to the invention, the tablet or granulate may consist of abrasive media together with other components.

Further, according to the invented system for dissolving a tablet or granulate, the receptacle may also be designed as a disk-like structure. According to the invention, the system for dissolving a tablet or granulate may provide that the receptacle is fused in order to form a mounting ring around the edge or circumference of the disk.

Further, according to the invented system, the clearance or space between the side of the tablet, or the equivalent extent of the granulate, and the receptacle be between $1/20^{th}$ and $1/10^{th}$ of its diameter.

Also according to the invention, the system for dissolving a tablet or granulate may provide, that the natural resonance of the receptacle when submerged in water lie between 60 and 100 Hertz.

Also according to the invention, the system for dissolving a tablet or granulate may provide that the receptacle or the mesh be sized so that the openings do not exceed 0.3 mm.

Also according to the invention, the system for dissolving a tablet or granulate may provide, that the thread or diameter of the woven wire lie between 0.12 mm and 0.25 mm.

Further, according to the invention, the system for dissolving a tablet or granulate may provide that the receptacle or the woven structure be made of nylon or of a similar thermoplastic material.

In addition, according to the invention, the system for dissolving a tablet or granulate may provide that the receptacle or the woven structure be made of a bio-plastic, e.g. from cellulose acetate or lactic acids.

Further, according to the invention, the system for dissolving a tablet or granulate may provide that the multiple openings inside the receptacle or the fabric structure should produce multiple turbulences.

In addition, according to the invention, the system for dissolving a tablet or granulate may provide, the flow of water through the device produce vibrations which enhance or boost the disintegration of the tablet and the release of abrasive media into the outflowing watery mixture.

Finally, according to the invention, the system for dissolving a tablet or granulate may provide that the receptacle or the woven structure cause or effect a continuous delivery of abrasive media into the water so that a homogeneous stream of a watery or fluid mixture results.

In order to dissolve cleansing tablets completely, the invention proposes a dispersing chamber in which the tablet is washed from all sides in a rotating swirl of water.

Increasingly tablets are being prepared to add desired compounds to the water or media stream in cleaning devices, but also in irrigation systems and disinfection devices. These are placed in a dispersing chamber in which they are intended to be dissolved by the stream of water or other media directed to them.

It is possible to accomplish this dissolution completely, however, with the commitment of correspondingly large volumes of water. Because the amount of the compounds dissolved in the medium decreases as the tablet becomes smaller, the cleansing effect is correspondingly less and the cleaning activity is often ended. In such cases a remnant of the tablet remains in the dispersing chamber and is then difficult to remove.

The reason for this is—in addition to the unavoidable reduction in the size of the removable area—that changing turbulence zone develop in the dispersion chamber and inevitably create dead zones as a consequence. These have no flow-through and collect deposits on their walls and in their corners as a result. This requires the regular cleaning of the mixing chamber or flushing with large volumes of water, even when these are not otherwise called for. This applies to an even greater degree to cleansers with abrasive components, which are as a rule insoluble in water and therefore inclined to collect in dead zones. This is especially critical in the case of applications in which the media must be forced through narrow nozzles in order to achieve the desired cleansing effect, since comparatively smaller volumes of flow are in play.

There have been numerous suggestions advocating dental cleansing with plaque removal by means of cleansers delivered by a stream of water, some of which involved abrasive media.

Most of the suggestions so far have involved the use of compressed air either to blast the powdered abrasive agent directly onto the teeth or to surround or mix it with a stream of water to control the dust or to use compressed air to spray a mixture of abrasive and carrier medium onto the teeth.

This is an obvious solution for dental practices because compressed air used to drive drills and clean equipment is already present. For daily dental hygiene seeking to remove plague and bio-film, the effort and expense would be disproportionately great.

Nevertheless, it is desirable to remove bio-films and deposits, which a toothbrush can only accomplish in a rough way, with a gentle abrasive medium each day. Because such a process is gentler than cleaning with a brush and creates, thanks to the smooth surfaces of the teeth, a pleasant, hygienic impression when the tongue is run over them.

The invention proposes to deliver a dispersing chamber for cleansing tablets which inhibits known disadvantages such as deposits, clogging, etc. and allows for a complete release of a cleansing compound.

The tablet should be continuously washed from all sides, even as it becomes smaller as the outer layers are dispersed, without breaking apart until the very end.

This is achieved firstly by means of a dispersing chamber which supports a flushing of the tablet from all sides. In addition, the inflowing stream of medium is made turbulent by means of a swirl chamber.

Even wearing away of the tablet is accomplished by placing it on a finger-like, slightly spiraling, elastic plastic holder just under a covering sieve. When inserted, the tablet is gently pressed into this holder and it will then be pushed by the spiraling fingers loosely against the sieve and kept in this orientation even as the tablet becomes smaller. The tablet begins to vibrate thanks to the turbulent flushing action and the outgassing of the splitting agent. The vibration causes the tablet to rotate on the spiraling fingers so that the entire surface is exposed to the liquid as it revolves. This will guarantee a steady and complete dispersal of the tablet's components into a specific volume of water. In the case of one possible design for the system, the water or medium stream may enter a feed chamber for the dispersing chamber through a lower inlet port. There it will pass through a cavitation device with slant-drilled intake ports before reaching the swirl chamber where it will engage the tablet lying on finger-shaped supports. The medium will thus wash the tablet from all sides and dissolve it correspondingly before exiting the swirl chamber through the sieve into a transfer chamber and from there into an outflow port.

A dispersing chamber designed in accordance with this invention may accomplish the steady disintegration of cleansing tablets containing abrasives and components that are difficult or impossible to dissolve in the medium which receives them by adding turbulent spinning motion to the medium through a turbulator placed ahead of the dispersing chamber.

In a dispersing chamber designed in accord with the invention to guarantee the uniform disintegration of cleansing tablets, the turbulator may consist of a cylinder which imparts a rotating motion to the entering medium by means of segmenting drill-holes in the cylinder wall In a dispersing chamber designed in accord with the invention to guarantee the uniform disintegration of cleansing tablets, the drill-holes in the turbulator may be horizontal and vertical in a 45° angle to the cylinder axis.

In a dispersing chamber designed in accord with the invention to guarantee the uniform disintegration of cleansing tablets, the tablet may rest on a holder consisting of elastic plastic fingers arranged in a spiral pattern.

In a dispersing chamber designed in accord with the invention to guarantee the uniform disintegration of cleansing tablets, the outflow port from the dispersing chamber may be closed by a sieve which acts as a filter.

In a dispersing chamber designed in accord with the invention to guarantee the uniform disintegration of cleansing tablets, the pressure of the medium flowing into the dispersing chamber may lie between 4 and 10 bar.

To deter clogging by abrasive particles, a nozzle designed according to the invention for the purpose of blasting a fluid cleanser containing dispersed abrasive particles may have a specific flexibility so that at the microscopic level it will be sufficiently malleable that eigen-vibration caused by the flow-through of the medium under high pressure inhibits the deposit of particles at its edges or detaches any occasional deposits.

In addition, the nozzle may include a turbulator ahead of the throat to impart a circular spin to the medium, in contrast then smooth walls in the compression chamber and in the nozzle channel and a circular flaring of 45° at the mouth.

Previous nozzle constructions for blasting tools are made of the hardest available material as a rule in order to lessen wear. Known designs are expensive to manufacture, often have a complicated construction and fail to sufficiently inhibit deposits and clogging.

Another factor having an influence with regard to possible clogging is the geometry of the nozzle. While it is obvious on one hand that dead zones are to be avoided because deposits accumulate there which are then all but impossible to remove due to an insufficient stream of the medium, it is nevertheless so that the turbulences which arise in the constriction of a jet channel and give rise to various different pressure zones and eddies have not been completely studied and are also not satisfactorily presentable in simulations.

On the other hand, just these are determining factors when it comes to the deposition of blasting agents on the walls of lines and nozzles.

The present invention proposes to construct nozzles cost effectively that they avoid clogging even when their diameter is only a little larger than the grain size of the solid components in the medium.

The material chosen for the nozzle must have a certain flexibility and be malleable at the microscopic level in order to prevent the deposit of particles on the walls by means of the eigen-vibration caused by the flow-through of the medium under high pressure. The same mechanism should remove any occasional short-term deposits. In addition, related experiments showed that wear and tear on nozzles was less under certain circumstances when they were made of a semi-flexible material.

Both of these apparently come about because the turbulences arising from the jet of medium being forced through the nozzle combined with any periodic irregularities in the primary pressure result in resonance effects which in turn cause the nozzle to vibrate and prevent deposits from occurring or detach any occasional build-up.

Thus the present invention makes the usual expensive materials and involved construction methods unnecessary if the nozzle is make of the plastic PMMA, for example. In addition, these may be made to be easily changed out—and as a result of the low cost—also replaced as necessary.

A the same time it proved advantageous for nozzles designed for abrasive ingredients as discussed above to have a primary pressure of from 5 to 9 bar, and to have the function areas for swirling and throw pattern so arranged that the medium is first swirled and then undergoes compression and exhaust in structures whose walls are as smooth as possible.

In this case a rotating turbulence is advantageous if it begins just before the compression zone and is followed then by a smooth jet channel as far as the nozzle mouth which again should have a 45° angle circular to the axis by a material thickness of at least 0.5 mm.

According to the invention, a line to the nozzle unit, which is contained in a sleeve, feeds the medium through drill-holes or vents in a filter plate into a pressure chamber where it encounters a cone-shaped spinner means held in place by a post and surrounded by a similarly cone-shaped housing and which presses the medium into the actual nozzle. Specifically for the purpose of dental cleansing with abrasive materials, the jet is widened out again at the mouth of the nozzle.

Alternatively, the spinner means may have the form of a cylinder and have drill-bit-like notches to effect a rotating swirling of the medium which with its abrasive materials then enters the pressure chamber which opens into the nozzle unit.

According to the invention, the nozzle for jet blasting with media containing abrasive ingredients may be made of a semi-rigid plastic such as polymethyl methacylate (PMMA) or hard PVC.

According to the invention, the nozzle for jet blasting with media containing abrasive ingredients may be a spiral-shaped spinner means placed ahead of the point where the medium enters the pressure zone.

According to the invention, the nozzle for jet blasting with media containing abrasive ingredients may have a conically tapering spinner means with from 15° to 25° to the axis.

According to the invention, the nozzle for jet blasting with media containing abrasive ingredients may permit the spiral path of the spinner means to have (±1) as many turns as its diameter in millimeters at its thickest point.

According to the invention, the nozzle for jet blasting with media containing abrasive ingredients may have a compression zone behind the spinner means with a circular tapering of the walls at an angle on both sides of from 15° to 20° to the nozzle axis.

According to the invention, the nozzle for jet blasting with media containing abrasive ingredients may have a nozzle tube that runs in a straight line from the end of the compression zone to the widening of the end of the tube at its exit (mouth).

According to the invention, the nozzle for jet blasting with media containing abrasive ingredients may have a mouth (discharge area) with a widening on both sides of from 20° to 25° to the nozzle axis.

According to the invention, the nozzle for jet blasting with media containing abrasive ingredients may have walls a maximum of 1 millimeter thick.

According to the invention, the nozzle for jet blasting with media containing abrasive ingredients may have walls in the nozzle tube and in the pressure and discharge areas that are smooth.

The invention claimed is:

1. A dental hygiene system that discharges a liquid containing particles dispersed from a solid dental cleansing compound for impinging the particles against the teeth of a user, the system comprising:
   a dispersing device comprising a housing, the housing comprising an inlet for connection to a source of liquid, a discharge for discharge of the liquid from the housing, and a fluid line extending through the housing fluidly connecting the inlet and the discharge to flow a liquid stream through the housing from the inlet to the discharge, the fluid line defining a downstream direction from the inlet to the discharge and an opposite upstream direction, a portion of the fluid line defining a dispersing chamber having an interior volume to receive the solid dental cleansing compound in the dispersing chamber, the dispersing chamber having a downstream side, a first body in the dispersing chamber disposed on the downstream side of the dispersing chamber, the first body having a plurality of openings that allow particles of a predetermined maximum size to pass through the first body, and a holder in the fluid line that obstructs upstream movement of the solid dental cleansing compound in the dispersing chamber;
   the dispersing chamber is configured to receive the solid dental cleansing compound and to provide clearance between the dispersing chamber and the solid dental cleansing compound when the solid dental cleansing compound is centered in the liquid stream to enable liquid flowing through the dispersing chamber to wet all sides of the solid dental cleansing compound;
   the holder comprises at least one member, the at least one member being at least semi-elastic and generating a force to locate the solid dental cleansing compound in the dispersing chamber, the force being applied to the solid dental cleansing compound and pressing the solid dental cleansing compound against the first body when the solid dental cleansing compound is in the dispersing chamber; and
   the holder permits displacement of the solid dental cleansing compound with respect to the holder when the solid dental cleansing compound is in the dispersing chamber to permit movement of the solid dental cleansing compound in the liquid stream caused by liquid flowing past the solid dental cleansing compound.

2. The dental hygiene system of claim 1 wherein the dispersing device is configured to generate a spiraling flow of liquid through the dispersing chamber.

3. The dental hygiene system of claim 1 wherein when the inlet of the dispersing device is fluidly connected to a source of liquid, the pressure of the liquid at the inlet is between 4 and 10 bar.

4. The dental hygiene system of claim 1 comprising a nozzle fluidly connected to the discharge of the dispersing device and a control device selectively operable to start and stop flow of liquid through the nozzle.

5. The dental hygiene system of claim 1 comprising a tank for holding the source of liquid, the tank contained in the housing of the dispersion device.

6. The dental hygiene system of claim 1 wherein the at least one member is disposed upstream from the first body.

7. The dental hygiene system of claim 6 wherein the at least one member is a pedestal having a surface that supports an upstream side of the solid dental cleansing compound when the solid dental cleansing compound is in the dispersing chamber.

8. The dental hygiene system of claim 6 wherein the at least one member comprises a second body disposed on an upstream side of the dispersing chamber, the second body having a plurality of openings that allow the liquid stream to pass through the second body.

9. The dental hygiene system of claim 1 wherein the at least one member comprises a plurality of elongate members, the members spaced apart from one another wherein liquid flowing through the fluid line flows between the members.

10. The dental hygiene system of claim 9 wherein the plurality of elongate members each comprise a surface, the surfaces of the elongate members cooperatively supporting an upstream side of the solid dental cleansing compound when the solid dental cleansing compound is in the dispersing chamber.

11. The dental hygiene system of claim 1 wherein he the at least one member comprises a second body, the second body having a plurality of openings that allow the liquid stream to pass through the second body, the second body attached to the first body, the first and second bodies forming a receptacle that receives the solid dental cleansing compound when the solid dental cleansing compound is in the dispersing chamber, and the receptacle provides annular clearance between the receptacle and the solid dental cleansing compound when the solid dental cleansing compound is centered in the liquid stream.

12. The dental hygiene system of claim 11 wherein the receptacle is elastically deformable.

13. The dental hygiene system of claim 11 wherein the first and second bodies are each made from a woven material, a mesh, a net, or a grid structure.

14. The dental hygiene system of claim 11 wherein the first and second bodies are each made from metal, plastic, fiber glass, fleece, cloth fabric, or blends thereof.

15. The dental hygiene system of claim 11 wherein the first body has first-sized openings and the second body has second-sized openings, the second-sized openings larger or smaller than the first-sized openings.

16. The dental hygiene system of claim 11 wherein the holder comprises a ledge that runs around the dispersing chamber, the receptacle comprising a rim supportable on the ledge.

17. The dental hygiene system of claim 1 wherein the at least one member is a coil spring.

18. The dental hygiene system of claim 17 wherein the coil spring is disposed downstream from the first body.

19. The dental hygiene system of claim 18 wherein the holder comprises a base member, the coil spring urging the base member against the housing.

20. The dental hygiene system of claim 17 wherein the coil spring is disposed upstream from the first body.

21. The dental hygiene system of claim 20 wherein the holder comprises a second body being disposed between the coil spring and the first body, the second body having a plurality of openings that permit the liquid stream to flow through the second body, the solid dental cleansing compound being between the first and second bodies when the solid dental cleansing compound is in the dispersing chamber, the coil spring urging the second body towards the first body.

22. The dental hygiene system of claim 21 wherein the holder comprises a base member, the coil spring urging the base member against the housing.

23. The dental hygiene system of claim 1 wherein the at least one member comprises a pair of coil springs, the solid dental cleansing compound being disposed between the pair of coil springs when the solid dental cleansing compound is in the dispersing chamber.

24. The dental hygiene system of claim 1 wherein the at least one member comprises an annular wall surrounding the dispersing chamber and one or more arms extending into the dispersing chamber from the annular wall, gaps being disposed between the one or more arms.

25. The dental hygiene system of claim 24 wherein the one or more arms comprises a plurality of arms spaced apart from one another, each arm being spiral-shaped.

26. The dental hygiene system of claim 1 wherein the at least one member comprises a second body, each of the first and second bodies being a disk-shaped body having an outer edge, the outer edges of the first and second bodies being joined together, the first and second bodies being elastically deformable.

* * * * *